United States Patent [19]

Zeller

[11] Patent Number: 5,728,875

[45] Date of Patent: Mar. 17, 1998

[54] MICROBICIDES

[75] Inventor: Martin Zeller, Baden, Switzerland

[73] Assignee: Novartis Corporation, Summit, N.J.

[21] Appl. No.: 703,300

[22] Filed: Aug. 26, 1996

Related U.S. Application Data

[62] Division of Ser. No. 431,230, Apr. 28, 1995, Pat. No. 5,585,519.

[30] Foreign Application Priority Data

May 4, 1994 [CH] Switzerland .................. 1407/94
Mar. 1, 1995 [CH] Switzerland .................. 584/95

[51] Int. Cl.$^6$ ............ C07C 233/76; C07C 303/35; C07C 303/40; A61K 31/18

[52] U.S. Cl. ............ 564/79; 514/424; 514/542; 514/600; 514/601; 514/605; 548/542; 560/9; 560/13; 564/99; 564/100; 564/189; 564/191; 564/196

[58] Field of Search ............ 564/79, 99, 100, 564/189, 191, 196; 548/542; 560/9, 13; 514/424, 542, 600, 601, 605

[56] References Cited

U.S. PATENT DOCUMENTS

| | | | |
|---|---|---|---|
| 5,081,284 | 1/1992 | Higucki et al. | 560/159 |
| 5,155,136 | 10/1992 | Welter et al. | 514/60 |
| 5,158,962 | 10/1992 | Seitz et al. | 514/335 |
| 5,210,084 | 5/1993 | Wallweber et al. | 514/237.5 |
| 5,254,715 | 10/1993 | Picard et al. | 560/13 |
| 5,278,148 | 1/1994 | Branca et al. | 574/19 |
| 5,371,267 | 12/1994 | Seitz et al. | 560/27 |

FOREIGN PATENT DOCUMENTS

| | | |
|---|---|---|
| 0493683 | 7/1992 | European Pat. Off. |
| A496239 | 7/1992 | European Pat. Off. |
| A550788 | 7/1993 | European Pat. Off. |
| A554729 | 8/1993 | European Pat. Off. |

OTHER PUBLICATIONS

Derwent Abstracts, (May, 1992)—073183 [10] (4026966).
Derwnet Abstracts, (Mar., 1993)—250662 [32] (Ep. 554729).
Derwent Abstracts, (Mar., 1992)—251485 [31] (Ep. 496239).
Derwent Abstracts, (Jul., 1992)—168045 [21] (Ep. 40305851).

*Primary Examiner*—Peter O'Sullivan
*Attorney, Agent, or Firm*—Michael P. Morris; Kevin T. Mansfield; Edward McC. Roberts

[57] ABSTRACT

α-Amino acid amides of the formula I

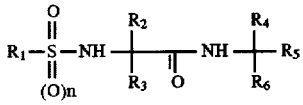

in which n is the number zero or one;

$R_1$ is $C_1-C_{12}$alkyl, which is unsubstituted or can be substituted by $C_1-C_4$alkoxy, $C_1-C_4$alkylthio, $C_1-C_4$alkylsulfonyl, $C_3-C_8$cycloalkyl, cyano, $C_1-C_6$alkoxycarbonyl, $C_3-C_6$alkenyloxycarbonyl or $C_3-C_6$alkynyloxycarbonyl; $C_3-C_8$cycloalkyl; $C_2-C_{12}$alkenyl;

$C_2-C_{12}$alkynyl; $C_1-C_{12}$halogenoalkyl or a group $NR_{13}R_{14}$; in which $R_{13}$ and $R_{14}$ independently of one another are hydrogen or $C_1-C_6$alkyl or together are tetra- or pentamethylene;

$R_2$ and $R_3$ independently of one another are hydrogen; $C_1-C_8$alkyl; $C_1-C_8$alkyl which is substituted by hydroxyl, $C_1-C_4$alkoxy, mercapto or $C_1-C_4$alkylthio; $C_3-C_8$alkenyl;

$C_3-C_8$alkynyl; $C_3-C_8$cycloalkyl or $C_3-C_8$cycloalkyl-$C_1-C_4$alkyl, or in which the two groups $R_2$ and $R_3$, together with the carbon atom to which they are bonded, form a three- to eight-membered carbocyclic ring;

$R_4$ is hydrogen or $C_1-C_6$alkyl;

$R_5$ is hydrogen; $C_1-C_6$alkyl or phenyl, which is unsubstituted or can be substituted by halogen, nitro, $C_1-C_4$alkyl, $C_1-C_4$halogenoalkyl, $C_1-C_4$alkoxy or $C_1-C_4$alkylthio; and $R_6$ is a group G

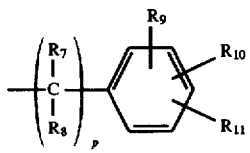

in which $R_7$ and $R_8$ independently of one another are hydrogen or $C_1-C_6$alkyl;

p is the number zero or one; and $R_9$, $R_{10}$ and $R_{11}$ independently of one another are hydrogen, $C_1-C_6$alkyl.

$C_1-C_6$halogenoalkyl, $C_3-C_6$alkenyl, $C_3-C_6$alkynyl, $C_1-C_6$alkoxy, $C_3-C_6$alkenyloxy, $C_3-C_6$alkynyloxy, $C_3-C_6$alkylthio, halogen or nitro are valuable microbicides. They can be employed in crop protection in the form of suitable compositions, for example for controlling fungal diseases.

3 Claims, No Drawings

MICROBICIDES

This is a division of application Ser. No. 08/431,230 filed Apr. 28, 1995 now U.S. Pat. No. 5,585,519.

The present invention relates to novel α-amino acid amides of the following formula I. It relates to the preparation of these substances and to agrochemical compositions which comprise at least one of these compounds as the active ingredient. The invention also relates to the preparation of the compositions mentioned and to the use of the active ingredients or compositions for controlling or preventing infestation of plants by phytopathogenic microorganisms, preferably fungi.

The compounds according to the invention are those of the general formula I

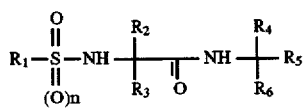

in which the substituents are defined as follows:

n is the number zero or one;

$R_1$ is $C_1-C_{12}$alkyl, which is unsubstituted or can be substituted by $C_1-C_4$alkoxy, $C_1-C_4$alkylthio, $C_1-C_4$alkylsulfonyl, $C_3-C_8$cycloalkyl, cyano, $C_1-C_6$alkoxycarbonyl, $C_3-C_6$alkenyloxycarbonyl or $C_3-C_6$alkynyloxycarbonyl; $C_3-C_8$cycloalkyl; $C_2-C_{12}$alkenyl;

$C_2-C_{12}$alkynyl; $C_1-C_{12}$halogenoalkyl or a group $NR_{13}R_{14}$; in which $R_{13}$ and $R_{14}$ independently of one another are hydrogen or $C_1-C_6$alkyl or together are tetra- or pentamethylene;

$R_2$ and $R_3$ independently of one another are hydrogen; $C_1-C_8$alkyl; $C_1-C_8$alkyl which is substituted by hydroxyl, $C_1-C_4$alkoxy, mercapto or $C_1-C_4$alkylthio; $C_3-C_8$alkenyl;

$C_3-C_8$alkynyl; $C_3-C_8$cycloalkyl or $C_3-C_8$cycloalkyl-$C_1-C_4$alkyl, or in which the two groups $R_2$ and $R_3$, together with the carbon atom to which they are bonded, form a three- to eight-membered carbocyclic ring;

$R_4$ is hydrogen or $C_1-C_6$alkyl;

$R_5$ is hydrogen; $C_1-C_6$alkyl or phenyl, which is unsubstituted or can be substituted by halogen, nitro, $C_1-C_4$alkyl, $C_1-C_4$halogenoalkyl, $C_1-C_4$alkoxy or $C_1-C_4$alkylthio; and $R_6$ is a group G

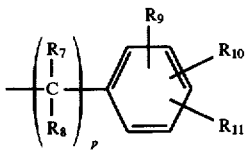

in which $R_7$ and $R_8$ independently of one another are hydrogen or $C_1-C_6$alkyl;

p is the number zero or one; and $R_9$, $R_{10}$ and $R_{11}$ independently of one another are hydrogen, $C_1-C_6$alkyl, $C_1-C_6$halogenoalkyl, $C_3-C_6$alkenyl, $C_3-C_6$alkynyl, $C_1-C_6$alkoxy, $C_3-C_6$alkenyloxy, $C_3-C_6$alkynyloxy, $C_1-C_6$alkylthio, halogen or nitro.

An important group is formed by compounds of the formula I in which n is the number zero or one;

$R_1$ is $C_1-C_{12}$alkyl; $C_1-C_{12}$alkyl which is substituted by $C_1-C_4$alkoxy, $C_1-C_4$alkylthio or $C_1-C_4$alkylsulfonyl; $C_2-C_{12}$alkenyl; $C_2-C_{12}$alkynyl; $C_1-C_{12}$halogenoalkyl or a group $NR_{13}R_{14}$; in which $R_{13}$ and $R_{14}$ independently of one another are $C_1-C_6$alkyl or together are tetra- or pentamethylene;

$R_2$ and $R_3$ independently of one another are hydrogen; $C_1-C_8$alkyl; $C_1-C_8$alkyl which is substituted by hydroxyl, $C_1-C_4$alkoxy, mercapto or $C_1-C_4$alkylthio; $C_3-C_8$alkenyl;

$C_3-C_8$alkynyl; $C_3-C_8$cycloalkyl; or $C_3-C_8$cycloalkyl-$C_1-C_4$alkyl, or in which the two groups $R_2$ and $R_3$, together with the carbon atom to which they are bonded, form a three- to eight-membered carbocyclic ring;

$R_4$ is hydrogen or $C_1-C_6$alkyl;

$R_5$ is hydrogen; $C_1-C_6$alkyl or phenyl, which is unsubstituted or substituted by halogen, nitro, $C_1-C_4$alkyl, $C_1-C_4$halogenoalkyl, $C_1-C_4$alkoxy or $C_1-C_4$alkylthio; and $R_6$ is a group G:

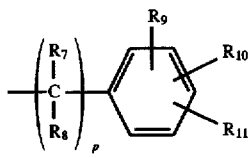

in which $R_7$ and $R_8$ independently of one another are hydrogen or $C_1-C_6$alkyl;

p is the number zero or one; and $R_9$, $R_{10}$ and $R_{11}$ independently of one another are hydrogen, $C_1-C_6$alkyl, $C_1-C_6$halogenoalkyl, $C_3-C_6$alkenyl, $C_3-C_6$alkynyl, $C_1-C_6$alkoxy, $C_3-C_6$alkenyloxy, $C_3-C_6$alkynyloxy, $C_1-C_6$alkylthio, halogen or nitro (sub-group A).

An important group is formed by compounds of the formula I in which n is the number zero or one and $R_1$ is $C_1-C_{12}$alkyl; $C_1-C_{12}$alkyl which is substituted by $C_1-C_4$alkoxy, $C_1-C_4$alkylthio or $C_1-C_4$alkylsulfonyl; $C_2-C_{12}$alkenyl; $C_1-C_{12}$halogenoalkyl or a group $NR_{13}R_{14}$; in which $R_{13}$ and $R_{14}$ independently of one another are $C_1-C_6$alkyl, or $R_{13}$ and $R_{14}$ together are tetra- or pentamethylene;

$R_2$ is hydrogen;

$R_3$ is $C_1-C_8$alkyl; $C_1-C_8$alkyl which is substituted by hydroxyl, $C_1-C_4$alkoxy, mercapto or $C_1-C_4$alkylthio; or $C_3-C_8$cycloalkyl;

$R_4$ is hydrogen;

$R_5$ is phenyl, which is unsubstituted or substituted by halogen, nitro, $C_1-C_4$alkyl, $C_1-C_4$halogenoalkyl, $C_1-C_4$alkoxy or $C_1-C_4$alkylthio and $R_6$ is a group G in which p is the number zero; and $R_9$, $R_{10}$ and $R_{11}$ independently of one another are hydrogen, $C_1-C_6$alkyl, $C_1-C_6$halogenoalkyl, $C_1-C_6$alkoxy, $C_3-C_6$alkenyloxy, $C_3-C_6$alkynyloxy, halogen or nitro (sub-group B).

Compounds of the formula I which are of particular importance are those in which n is the number zero or one;

$R_1$ is $C_1$–$C_{10}$alkyl; $C_1$–$C_4$halogenoalkyl; $C_2$–$C_6$alkenyl; $C_5$–$C_6$cycloalkyl; $C_1$–$C_6$alkyl which is substituted by cyano or $C_1$–$C_4$alkoxycarbonyl, or $C_1$–$C_2$dialkylamino;

$R_2$ is hydrogen;

$R_3$ is $C_2$–$C_5$alkyl or $C_3$–$C_6$cycloalkyl;

$R_4$ is hydrogen;

$R_5$ is phenyl, which is unsubstituted or substituted by halogen; and $R_6$ is a group G, in which p is the number zero;

$R_9$ is hydrogen; and $R_{10}$ and $R_{11}$ independently of one another are hydrogen or halogen (sub-group AA).

Another important group is formed by compounds of the formula I in which n is the number zero or one and $R_1$ is $C_1$–$C_{10}$alkyl; $C_1$–$C_4$halogenoalkyl; $C_2$–$C_6$alkenyl, or $C_1$–$C_2$dialkylamino;

$R_2$ is hydrogen;

$R_3$ is $C_2$–$C_5$alkyl or $C_3$–$C_6$cycloalkyl;

$R_4$ is hydrogen;

$R_5$ is phenyl, which is unsubstituted or substituted by halogen, and $R_6$ is a group G in which p is the number zero;

$R_9$ is hydrogen; and $R_{10}$ and $R_{11}$ independently of one another are hydrogen or halogen (sub-group C).

Among these compounds, those in which n is the number one are preferred (sub-group Ca).

Compounds of sub-group C which are also preferred are those in which n has the value one and $R_3$ is $C_3$–$C_4$alkyl (sub-group Cd).

Important compounds of the sub-group AA within the scope of formula I are those in which n has the value one; and $R_1$ is methyl, ethyl, vinyl, cyclopentyl, cyclohexyl or dimethylamino (sub-group AAa).

Another preferred group is formed by compounds of the formula I in which $R_1$ is $C_1$–$C_{12}$alkyl; $C_3$–$C_8$cycloalkyl; $C_1$–$C_{12}$alkyl which is substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_1$–$C_6$alkynyloxycarbonyl; $C_2$–$C_{12}$alkenyl;

$C_1$–$C_{12}$halogenoalkyl or a group $NR_{13}R_{14}$; in which $R_{13}$ and $R_{14}$ independently of one another are hydrogen or $C_1$–$C_6$alkyl or together are tetra- or pentamethylene;

$R_2$ is hydrogen;

$R_3$ is $C_1$–$C_8$alkyl; $C_1$–$C_8$alkyl which is substituted by hydroxyl, $C_1$–$C_4$alkoxy, mercapto or $C_1$–$C_4$alkylthio; or $C_3$–$C_8$cycloalkyl;

$R_4$ is hydrogen or $C_1$–$C_4$alkyl;

$R_5$ is hydrogen; or $C_1$–$C_6$alkyl; and $R_6$ is a group G in which $R_7$ and $R_8$ independently of one another are hydrogen or $C_1$–$C_4$alkyl;

p is the number one; and $R_9$, $R_{10}$ and $R_{11}$ independently of one another are hydrogen, $C_1$–$C_6$alkyl, $C_1$–$C_6$halogenoalkyl, $C_1$–$C_6$alkoxy, $C_3$–$C_6$alkenyloxy, $C_3$–$C_6$alkynyloxy or halogen (sub-group F).

Important compounds of sub-group C within the scope of formula I are those in which n is the number one and $R_1$ is methyl; ethyl; vinyl or dimethylamino (sub-group Cc).

An important sub-group is formed by compounds of the formula I in which n is the number zero or one and $R_1$ is $C_1$–$C_{12}$alkyl; $C_1$–$C_{12}$alkyl which is substituted by $C_1$–$C_4$alkoxy, $C_1$–$C_4$alkylthio or $C_1$–$C_4$alkylsulfonyl; $C_2$–$C_{12}$alkenyl; $C_1$–$C_{12}$halogenoalkyl or a group $NR_{13}R_{14}$; in which $R_{13}$ and $R_{14}$ independently of one another are $C_1$–$C_6$alkyl or together are tetra- or pentamethylene;

$R_2$ is hydrogen;

$R_3$ is $C_1$–$C_8$alkyl; $C_1$–$C_8$alkyl which is substituted by hydroxyl, $C_1$–$C_4$alkoxy, mercapto or $C_1$–$C_4$alkylthio; or $C_3$–$C_8$cycloalkyl;

$R_4$ is hydrogen or $C_1$–$C_4$alkyl;

$R_5$ is hydrogen or $C_1$–$C_6$alkyl and $R_6$ is a group G in which $R_7$ and $R_8$ independently of one another are hydrogen or $C_1$–$C_4$alkyl;

p is the number one; and $R_9$, $R_{10}$ and $R_{11}$ independently of one another are hydrogen, $C_1$–$C_6$alkyl, $C_1$–$C_6$halogenoalkyl, $C_1$–$C_6$alkoxy, $C_3$–$C_6$alkenyloxy, $C_3$–$C_6$alkynyloxy or halogen (sub-group D).

A preferred sub-group is formed by compounds of the formula I in which n is the number zero or one and the other substituents are defined as follows:

$R_1$ is $C_1$–$C_{10}$alkyl, $C_1$–$C_4$halogenoalkyl, $C_2$–$C_6$alkenyl or $C_1$–$C_2$dialkylamino;

$R_2$ is hydrogen;

$R_3$ is $C_2$–$C_5$alkyl or $C_3$–$C_6$cycloalkyl;

$R_4$ is hydrogen or $C_1$–$C_4$alkyl;

$R_5$ is hydrogen; and $R_6$ is a group G in which $R_7$ is hydrogen;

$R_8$ is hydrogen or $C_1$–$C_4$alkyl;

p is the number one; and $R_9$, $R_{10}$ and $R_{11}$ independently of one another are hydrogen, $C_1$–$C_6$alkyl, $C_1$–$C_6$halogenoalkyl, $C_1$–$C_6$alkoxy, $C_3$–$C_6$alkenyloxy, $C_3$–$C_6$alkynyloxy or halogen (sub-group E).

Preferred compounds of sub-group E are those in which n is the number one, $R_1$ is $C_1$–$C_{10}$alkyl, $C_1$–$C_4$halogenoalkyl, $C_2$–$C_4$alkenyl or $C_1$–$C_2$dialkylamino;

$R_9$ is hydrogen; and $R_{10}$ and $R_{11}$ are $C_1$–$C_6$alkoxy (sub-group Ea).

In this particularly preferred sub-group Ea, particular compounds of the formula I are those in which $R_1$ is $C_1$–$C_4$alkyl, $C_1$–$C_4$halogenoalkyl, vinyl or dimethylamino (sub-group Eab).

In the preferred sub-group Ea, compounds of the formula I which are furthermore preferred are those in which $R_3$ is $C_3$–$C_4$alkyl (sub-group Eaa).

Further preferred compounds of sub-group Ea are compounds of the formula I in which R$_4$ is hydrogen; and R$_6$ is a group G in which R$_7$ and R$_8$ are hydrogen;

p is the number one;

R$_9$ is hydrogen; and

R$_{10}$ and R$_{11}$ are C$_1$–C$_6$alkoxy (sub-group Eac).

In the particularly preferred sub-group Ea, preferred compounds of the formula I are those in which R$_{10}$ is C$_1$–C$_4$alkoxy in the p-position and R$_{11}$ is C$_1$–C$_4$alkoxy in the m-position (sub-group Ead).

Preferred compounds of sub-group Ead within the scope of the formula I are those in which R$_1$ is C$_1$–C$_4$alkyl; vinyl or dimethylamino;

R$_{10}$ is p-methoxy; and

R$_{11}$ is m-methoxy (sub-group Eada).

Important compounds within the scope of the formula I are those in which n is the number one; and R$_1$ is C$_1$–C$_{10}$alkyl; C$_1$–C$_4$halogenoalkyl; C$_2$–C$_4$alkenyl; C$_5$–C$_6$cycloalkyl; C$_1$–C$_4$alkyl which is substituted by cyano or C$_1$–C$_4$alkoxycarbonyl, or C$_1$–C$_2$dialkylamino;

R$_9$ is hydrogen; and

R$_{10}$ and R$_{11}$ are C$_1$–C$_6$alkoxy, C$_3$–C$_6$alkenyloxy or C$_3$–C$_6$alkynyloxy (sub-group H).

Preferred compounds of sub-group H are those in which

R$_1$ is C$_1$–C$_4$alkyl, C$_1$–C$_4$halogenoalkyl, vinyl, dimethylamino or C$_5$–C$_6$cycloalkyl (sub-group Ha).

Compounds which are furthermore preferred within the scope of the formula I are those in which R$_3$ is C$_3$–C$_4$alkyl (sub-group Hb).

A particularly preferred sub-group is formed by compounds within the scope of the formula I in which R$_{10}$ is p-C$_1$–C$_4$alkoxy, p-C$_3$–C$_4$alkenyloxy or p-C$_3$–C$_4$alkynyloxy; and R$_{11}$ is m-C$_1$–C$_4$alkoxy (sub-group Hc).

Important compounds of sub-group Hc are those in which

R$_1$ is C$_1$–C$_4$alkyl, vinyl or dimethylamino;

R$_{10}$ is p-methoxy, p-allyloxy or p-propargyloxy; and

R$_{11}$ is m-methoxy (sub-group Hca).

Particularly important compounds of sub-group Hca are those in which

R$_{10}$ is p-methoxy and

R$_{11}$ is m-methoxy (sub-group Hcb).

In the above formula I "halogen" includes fluorine, chlorine, bromine and iodine.

The alkyl, alkenyl and alkynyl radicals can be straight-chain or branched, and this also applies to the alkyl, alkenyl, or alkynyl moiety of the halogenoalkyl, alkylsulfonylalkyl, alkenyloxy, alkynyloxy, alkoxy and alkylthio group and other groups.

Alkyl itself or as a constituent of another substituent is to be understood as meaning, for example, depending on the number of carbon atoms mentioned, methyl, ethyl, propyl, butyl, pentyl, dodecyl and their isomers, for example isopropyl, isobutyl, tert-butyl or sec-butyl. Depending on the number of carbon atoms mentioned, cycloalkyl is cyclopropyl, cyclobutyl, cyclopentyl, cyclohexyl, cycloheptyl or cyclooctyl.

A halogenoalkyl group can contain one or more (identical or different) halogen atoms, for example CHCl$_2$, CH$_2$F, CCl$_3$, CH$_2$Cl, CHF$_2$, CF$_3$, CH$_2$CH$_2$Br, C$_2$Cl$_5$, CH$_2$Br, CHBrCl and the like.

The presence of at least one asymmetric carbon atom and/or at least one asymmetric sulfur atom in the compounds of the formula I means that the compounds can occur in optically isomeric forms. Geometric isomerism can also occur due to the presence of an aliphatic —C═C— double bond. Formula I is intended to include all these possible isomeric forms as well as mixtures thereof.

Certain α-amino acid derivatives of a different type of structure have already been proposed for controlling plant-injurious fungi (for example in EP-398072, EP-425925, DE-4026966, EP-477639, EP-493683, DE-4035851, EP-487154, EP-496239, EP-550788 and EP-554729). However, the action of these preparations is not satisfactory. Surprisingly, novel microbicides having a high action have been found with the compound structure of the formula I. Description of processes for the preparation of compounds according to the invention The compounds of the formula I can be prepared a) by reaction of a substituted amino acid of the formula II

in which the radicals R$_1$, R$_2$ and R$_3$ and n are as defined above, or carboxy-activated derivatives thereof, in the presence or absence of a catalyst, in the presence or absence of an acid-binding agent and in the presence or absence of a diluent, with an amine of the formula III

in which R$_4$, R$_5$ and R$_6$ are as defined above.

The amino acid derivatives of the formula II required for carrying out process a) according to the invention are known per se or can be prepared by process aa) described below.

The amines of the formula III are generally known compounds of organic chemistry.

Carboxy-activated derivatives of the amino acid of the formula II are all the carboxy-activated derivatives, such as acid halides, for example acid chloride; and furthermore symmetric or mixed anhydrides, for example the mixed O-alkyl-carboxylic acid anhydrides; and moreover activated esters, for example p-nitrophenyl esters or N-hydroxysuccinimide esters, as well as activated forms of the amino acid which are produced in situ using condensation agents (for example dicyclohexylcarbodiimide or carbonyldiimidazole).

The acid halides corresponding to the amino acid of the formula II can be prepared by reacting the amino acid of the formula II with a halogenating agent, for example phosphorus pentachloride, thionyl chloride or oxalyl chloride, in a manner known per se. The mixed anhydrides corresponding to the amino acid of the formula II can be prepared by reacting the amino acid of the formula II with chloroformic acid esters, for example chloroformic acid alkyl esters, preferably either butyl chloroformate, in the presence or absence of an acid-binding agent, such as an inorganic or organic base, for example a tertiary amine, for example triethylamine, pyridine, N-methylpiperidine or N-methylmorpholine.

The reaction of the amino acid of the formula II or the carboxy-activated derivatives of the amino acid of the formula II with an amine of the formula III takes place in an inert diluent. Examples are: aromatic, non-aromatic or halogenated hydrocarbons, for example chlorohydrocarbons, for example methylene chloride or toluene; ketones, for example acetone; esters, for example ethyl acetate; amides, for example dimethylformamide; nitriles, for example acetonitrile, or ethers, for example tetrahydrofuran, dioxane, diethyl ether or tert-butyl methyl ether; or water or mixtures of these inert diluents. The acid-binding agents which may be present are (in)organic bases, for example an alkali metal or alkaline earth metal hydroxide or carbonate, for example sodium hydroxide, potassium hydroxide, sodium carbonate or potassium carbonate, or, for example, a tertiary amine, for example triethylamine, pyridine, N-methylpiperidine or N-methylmorpholine. The temperatures are −80° to +150° C., preferably −20° to +60° C.

Compounds of the formula I can also be prepared b) by reaction of a sulfonic acid derivative or sulfinic acid derivative of the formula IV

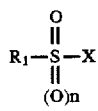

in which $R_1$ and n are as defined above and in which X is halogen (chlorine or bromine), the radical $R_1$—$SO_2$—O— or the radical $R_1$—SO—O—, with an amine of the formula V

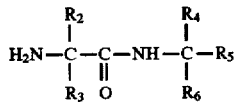

in which $R_2$, $R_3$, $R_4$, $R_5$ and $R_6$ are as defined above.

The sufonic acid derivatives or sulfinic acid derivatives of the formula IV required for process b) are known per se. The amines of the formula V which are likewise required are similarly known per se or can be prepared by processes bb) described below.

The reaction of the sulfonic acid derivatives or sulfinic acid derivatives of the formula IV with an amine of the formula V takes place in an inert diluent. Examples are: aromatic, non-aromatic or halogenated hydrocarbons, for example chlorohydrocarbons, for example methylene chloride or toluene; ketones, for example acetone; esters, for example ethyl acetate; amides, for example dimethylformamide; nitriles, for example acetonitrile, or ethers, for example tetrahydrofuran, dioxane, diethyl ether or tert-butyl methyl ether; or water or mixtures of these inert diluents. Acid-binding agents which may be present are (in)organic bases, for example an alkali metal or alkaline earth metal hydroxide or carbonate, for example sodium hydroxide, potassium hydroxide, sodium carbonate or potassium carbonate, or, for example, a tertiary amine, for example triethylamine, pyridine, N-methylpiperidine or N-methylmorpholine. The temperatures are −80° to +150° C., preferably −20° to +60° C.

Compounds of the formula I can also be prepared c) by oxidation of a compound of the formula I'

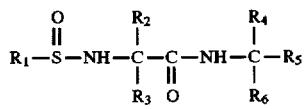

with an oxidizing agent, in which $R_1$, $R_2$, $R_3$, $R_4$, $R_5$ and $R_6$ are as defined above, with the proviso that none of the substituents $R_1$, $R_2$, $R_3$, $R_5$ or $R_6$ comprises a thiol or alkylthio group.

Oxidizing agents are either organic oxidizing agents, such as alkyl hydroperoxides, for example cumyl hydroperoxide, or inorganic oxidizing agents, such as peroxides, for example hydrogen peroxide, or such as transition metal oxides, for example chromium trioxide, and transition metal oxide salts, for example potassium permanganate, potassium dichromate or sodium dichromate.

The reaction of the compounds of the formula I' with the oxidizing agent takes place in an inert solvent, for example water or a ketone, for example acetone, or in mixtures thereof, in the presence or absence of an acid or in the presence or absence of a base, at temperatures of −80° to +150° C.

aa) The amino acid derivatives of the formula II required can be prepared by reaction of an amino acid of the formula VI

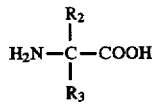

in which $R_2$ and $R_3$ are as defined above, with a sulfonic acid derivative or sulfinic acid derivative of the formula IV

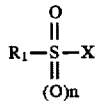

in which $R_1$ and n are as defined above and in which X is halogen (chlorine or bromine), the radical $R_1$—$SO_2$—O— or the radical $R_1$—SO—O—.

The sulfonic acid derivatives or sulfinic acid derivatives of the formula IV required for process aa) and the amino acids of the formula VI are known.

The solvents (or diluents), acid-binding agents and temperature range correspond to the statements for reaction a) or b).

bb) The amines of the formula V required can be prepared by acid hydrolysis of a compound of the formula VII

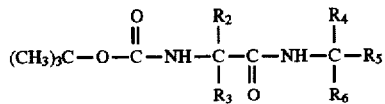

Compounds of the formula VII have been disclosed in the literature, for example in EP-398072, DE-4026966, EP-493683, EP-496239, EP-550788 and EP-554728.

The reaction of the compounds of the formula VII with an inorganic or organic acid, for example mineral acids (hydrogen halide acid or sulfuric acid) or carboxylic acids, for example acetic acid or trifluoroacetic acid, or sulfonic acids, for example methanesulfonic acid or p-toluenesulfonic acid, can be carried out in an inert diluent (hydrocarbons, for example methylene chloride or toluene; ketones, for example acetone; or water) at temperature of −40° to +150° C. If appropriate, mixtures of different acids and different diluents can also be employed. The acid itself is also capable of serving as the diluent.

The compounds of the formula I are oils or solids which are stable at room temperature and have valuable microbicidal properties. They can be employed preventively and curatively in the agricultural sector or in related areas for controlling plant-injurious microorganisms. The active ingredients of the formula I according to the invention not only have an outstanding microbicidal, in particular fungicidal, action, coupled with low use concentrations, but also are particularly well tolerated by plants.

Surprisingly, it has now been found that compounds of the formula I have a very favourable biocidal spectrum for practical requirements for controlling phytopathogenic microorganisms, in particular fungi. They have very advantageous curative and preventive properties and are employed for the protection of numerous crop plants. Using the active ingredients of the formula I, the pests occurring on plants or parts of plants (fruit, blossom, foliage, stems, tubers, roots) of different crops of useful plants can be checked or destroyed, parts of plants which grow on later, for example, also remaining protected from phytopathogenic fungi.

The novel active ingredients of the formula I prove to be preferentially active against specific genera of the fungal class of Fungi imperfecti (for example Cercospora, Botrytis, Helminthosporium, Fusarium Septoria, Pyricularia and Alternaria), Basidiomycetes (for example the genera Hemileia, Rhizoctonia and Puccinia) and Ascomycetes (for example Podosphaera, Monilinia, Uncinula, Cercosporella, Erysiphe and Venturia), Deuteromycetes (for example Rhynchosporium), and in particular against Oomycetes (for example Plasmopara, Peronospora, Pythium, Bremia and Phytophthora). They are therefore a valuable enrichment of compositions in crop protection for controlling phytopathogenic fungi. The compounds of the formula I furthermore can be employed as dressing agents for the treatment of seed (fruit, tubers, grains) and plant seedlings for protection against fungal infections and against phytopathogenic fungi which occur in the soil.

The invention also relates to compositions which comprise compounds of the formula I as active ingredient components, in particular crop protection compositions, and to their use in the agricultural sector or related areas.

The invention moreover also relates to the preparation of these compositions, which comprises intimate mixing of the active substance with one or more substances or substance groups described herein. The process for treatment of plants which comprises application of the novel compounds of the formula I or of the novel compositions is also included.

Target crops for the crop protection use disclosed herein are, in the context of this invention, for example, the following plant species: cereals (wheat, barley, rye, oats, rice, maize, sorghum, dinkel, triticale and related species); beet (sugar and feed beet); pome, stone and soft fruit (apples, pears, plums, peaches, almonds, cherries, strawberries, raspberries and blackberries); pulses (beans, lentils, peas, soya); oil crops (rape, mustard, poppy, olive, sunflower, coconut, castor, cacao, groundnut); cucumber plants (pumpkins, cucumbers, melons); fibre plants (cotton, flax, hemp, jute); citrus fruits (oranges, lemons, gapefruits, mandarines); types of vegetables (spinach, lettuce, asparagus, cabbage species, carrots, onions, tomatoes, potatoes, paprika); bay plants (avocado, cinnamonium, camphor) or plants such as tobacco, nuts, coffee, sugarcane, tea, pepper, vines, hops, banana and natural rubber plants and ornamentals.

Active ingredients of the formula I are usually used in the form of compositions and can be introduced onto the area or plant to be treated at the same time as or successively with other active ingredients. These other active ingredients can be either fertilizers, mediators of trace elements or other preparations which influence plant growth. It is also possible to use here selective herbicides as well as insecticides, fungicides, bactericides, nematicides, molluscicides or mixtures of several of these preparations, if appropriate together with other carriers, surfactants or other application-promoting additives customary in formulation technology.

Suitable carriers and additives can be solid or liquid and correspond to the substances used for this purpose in formulation technology, for example naturally occurring or regenerated mineral substances, solvents, dispersants, wetting agents, tackifiers, thickeners, binders or fertilizers.

A preferred method of application of an active ingredient of the formula I or of an agrochemical composition which comprises at least one of these active ingredients is application to the foliage (leaf application). The application frequency and rate of application depend on the danger of infestation by the pathogen in question. The compounds of the formula I can also be applied to plant propagation material (dressing of grains, fruit, tubers, shoots, seedlings, roots and the like), for example either by impregnating cereal grains (seed) or potato tubers or freshly cut shoots in a liquid composition of the active ingredient or coating them with a solid composition.

The compounds of the formula I are employed here in unchanged form or, preferably, together with the auxiliaries customary in formulation technology. For this purpose, they are expediently processed, for example, to emulsion concentrates, brushable pastes, directly sprayable or dilutable solutions, dilute emulsions, wettable powders, soluble powders, dusts or granules, by encapsulation in, for example, polymeric substances in a known manner. The methods of use, such as spraying, atomizing, dusting, scattering, brushing on or pouring, like the nature of the composition, are chosen according to the intended aims and the given circumstances.

Favourable rates of application are in general 5 g to 2 kg of active substance (AS) per hectare (ha), preferably 10 g to 1 kg of AS/ha, in particular 20 g to 600 g of AS/ha.

The formulations, i.e. the preparations, formulations or compositions comprising the active ingredient of the formula I and, if appropriate, a solid or liquid additive, are prepared in a known manner, for example by intimate mixing and/or grinding of the active ingredient with extenders, such as solvents, solid carriers and if appropriate surface-active compounds (surfactants).

Solvents are: aromatic hydrocarbons, preferably $C_8$ to $C_{12}$ fractions, such as xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol or ethylene glycol monomethyl or monoethyl ether, ketones, such as cyclohexanone, strongly polar solvents, such as N-methyl-2-pyrrolidone, dimethyl sulfoxide or dimethylformamide, and plant oils, which may be epoxidized, such as epoxidized coconut oil or soya oil, and water.

Solid carriers, for example for dusts and dispersible powders, are as a rule natural rock powders, such as calcite, talc, kaolin, montmorillonite or attapulgite. Highly disperse silicic acid or highly disperse absorbent polymers can also be added to improve the physical properties. Granular absorptive granule carriers are porous types, such as pummice, broken brick, sepiolite or bentonite, and nonsorptive carrier materials are, for example, calcite or sand. A large number of pregranulated materials of inorganic nature, such as dolomite or comminuted plant residues, can also be used.

Surface-active compounds are, depending on the nature of the active ingredient of the formula I to be formulated, nonionic, cationic and/or anionic surfactants with good emulsifying, dispersing and wetting properties. Surfactants are also to be understood as meaning surfactant mixtures.

Suitable anionic surfactants can be either so-called water-soluble soaps, or water-soluble synthetic surface-active compounds.

Examples of nonionic surfactants are nonylphenolpolyethoxyethanols, castor oil polyglycol ether, polypropylene/polyethylene oxide adducts, tributylphenoxypolyethylene-ethanol, polyethylene glycol and octylphenoxypolyethoxyethanol.

Fatty acid esters of polyoxyethylene sorbitan, such as polyoxyethylene sorbitan trioleate, can also be used.

The cationic surfactants are, in particular, quaternary ammonium salts which contain at least one alkyl radical having 8 to 22 C atoms as N substituents and lower, non-halogenated or halogenated alkyl, benzyl or lower hydroxyalkyl radicals as further substituents.

Other surfactants which are customary in formulation technology are known to the expert or can be found from the relevant technical literature.

The agrochemical preparations as a rule comprise 0.1 to 99 per cent by weight, in particular 0.1 to 95 per cent by weight, of active compound of the formula I, 99.9 to 1 per cent by weight, in particular 99.8 to 5 per cent by weight, of a solid or liquid additive and 0 to 25 per cent by weight, in particular 0.1 to 25 per cent by weight, of a surfactant.

While concentrated compositions tend to be preferred as commercial products, the end user as a rule uses dilute compositions.

The compositions can also comprise further additives, such as stabilizers, defoamers, viscosity regulators, binders or tackifiers, as well as fertilizers, trace element mediators or other preparations which influence plant growth, in order to achieve special effects.

The following examples illustrate the invention described above without limiting it in its scope in any manner. Temperatures are stated in degrees Celsius.

Preparation Examples for the Compounds of the Formula I

H-1.1.: (R,S)-2-(N,N-dimethylsulfamoyl)-amino-3-methyl-butyric acid N-(1,1-diphenylmethyl)-amide [Process a)]

[Compound 1.1]

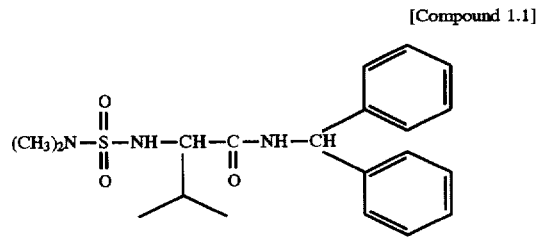

2.2 g of (R,S)-2-(N,N-dimethylsulfamoyl)-amino-3-methyl-butyric acid and 1.1 ml of N-methylmorpholine are cooled to $-10°$ C. in 50 ml of tetrahydrofuran, while stirring. 1.25 ml of isobutyl chloroformate are added dropwise and the reaction mixture is subsequently stirred at $-10°$ C. for 30 minutes. 1.7 ml of 1-amino-1,1-diphenylmethane are now added and the mixture is stirred at room temperature for 6 hours. The reaction mixture is introduced into 200 ml of 2N hydrochloric acid and extracted twice with 200 ml of ethyl acetate each time. The organic phases are washed once with 200 ml of 2N hydrochloric acid, once with 100 ml of saturated sodium chloride solution, twice with 200 m 1 of 2N potassium bicarbonate solution each time and once with 100 ml of saturated sodium chloride solution, dried over magnesium sulfate and concentrated. (R,S)-2-(N,N-dimethylsulfamoyl)-amino-3-methyl butyric acid N-(1,1-diphenylmethyl)-amide, which can be purified by recrystallization from ethyl acetate/hexane, is obtained, melting point $156°–158°$ C.

The compounds shown in Table 1 are obtained analogously to this example.

TABLE 1

(prepared according to process a))

$$R_1-\underset{\underset{(O)_n}{\|}}{\overset{\overset{O}{\|}}{S}}-NH-\underset{\underset{R_3}{|}}{\overset{\overset{R_2}{|}}{C}}-\underset{\underset{O}{\|}}{C}-NH-\underset{\underset{R_6}{|}}{\overset{\overset{R_4}{|}}{C}}-R_5 \quad (I)$$

2,3-D=2,3-dimethoxy-benzyl, 2,5-D=2,5-dimethoxy-benzyl, 3,4-D=3,4-dimethoxy-benzyl, 3,5-D=3,5-dimethoxy-benzyl, 3,4,5-T=3,4,5-trimethoxy-benzyl Stereochemistry on the α C atom of the amino acid (where known):

R,S for compounds 1.1 to 1.5,1.9,1.10,1.13 to 1.18

S for compounds 1.6 to 1.8,1.11,1.12,1.23 to 1.42,1.44, 1.45,1.49 to 1.83

| Comp. No. | $R_1$ | n | $R_2$ | $R_3$ | $R_4$ | $R_5$ | $R_6$ | Physical data m.p. °C. |
|---|---|---|---|---|---|---|---|---|
| 1.1 | Me₂N | 1 | H | 2-propyl | H | Phenyl | Phenyl | 156–158 |
| 1.2 | Me₂N | 1 | H | 2-propyl | H | H | 3,4-D | Oil |
| 1.3 | Methyl | 0 | H | 2-propyl | H | H | 3,4-D | |
| 1.4 | 2-Propyl | 0 | H | 2-propyl | H | H | 3,4-D | |
| 1.5 | 2-Methyl-2-propyl | 0 | H | 2-propyl | H | H | 3,4-D | |
| 1.6 | Methyl | 0 | H | 2-propyl | H | H | 3,4-D | |
| 1.7 | 2-Propyl | 0 | H | 2-propyl | H | H | 3,4-D | |

-continued

| Comp. No. | R₁ | n | R₂ | R₃ | R₄ | R₅ | R₆ | Physical data m.p. °C. |
|---|---|---|---|---|---|---|---|---|
| 1.8 | 2-Methyl-2-propyl | 0 | H | 2-propyl | H | H | 3,4-D | |
| 1.9 | Me₂N | 1 | H | Methyl | H | H | 3,4-D | |
| 1.10 | Methyl | 1 | H | Methyl | H | H | 3,4-D | |
| 1.11 | Me₂N | 1 | H | Ethyl | H | H | 3,4-D | 108–111 |
| 1.12 | Methyl | 1 | H | Ethyl | H | H | 3,4-D | |
| 1.13 | Me₂N | 1 | H | Cyclopropyl | H | H | 3,4-D | |
| 1.14 | Methyl | 1 | H | Cyclopropyl | H | H | 3,4-D | |
| 1.15 | Me₂N | 1 | H | Cyclopropyl-methyl | H | H | 3,4-D | |
| 1.16 | Methyl | 1 | H | Cyclopropyl-methyl | H | H | 3,4-D | |
| 1.17 | Me₂N | 1 | Me | 2-Propyl | H | H | 3,4-D | |
| 1.18 | Methyl | 1 | Me | 2-Propyl | H | H | 3,4-D | |
| 1.19 | Me₂N | 1 | Me | Methyl | H | H | 3,4-D | |
| 1.20 | Methyl | 1 | Me | Methyl | H | H | 3,4-D | 134–135 |
| 1.21 | Me₂N | 1 | Tetramethylene | | H | H | 3,4-D | |
| 1.22 | Methyl | 1 | Tetramethylene | | H | H | 3,4-D | 152–154 |
| 1.23 | Me₂N | 1 | H | 1-(2-Methyl-2-propoxy)-ethyl | H | H | 3,4-D | |
| 1.24 | Methyl | 1 | H | 1-(2-Methyl-2-propoxy)-ethyl | H | H | 3,4-D | |
| 1.25 | Ethyl | 1 | H | Ethyl | H | (S)-Me | Phenyl | 122–123 |
| 1.26 | Ethyl | 1 | H | Ethyl | H | H | 3,4-D | 107–109 |
| 1.27 | Ethyl | 1 | H | Ethyl | H | (R)-Me | Phenyl | 122–123 |
| 1.28 | Ethyl | 1 | H | Ethyl | H | Phenyl | Phenyl | 151–153 |
| 1.29 | Ethyl | 1 | H | 1-(2-Methyl-2-propoxy)-ethyl | H | H | 3,4-D | Oil |
| 1.30 | Ethyl | 1 | H | 1-(2-Methyl-2-propoxy)-ethyl | H | (R)-Me | Phenyl | 84–86 |
| 1.31 | Ethyl | 1 | H | 1-(2-Methyl-2-propoxy)-ethyl | H | (S)-Me | Phenyl | 138–139 |
| 1.32 | Ethyl | 1 | H | 1-(2-Methyl-2-propoxy)-ethyl | H | Phenyl | Phenyl | 115–116 |
| 1.33 | Ethyl | 1 | H | 2-Propyl | H | Methyl | 4-Cl-phenyl | 152–154 |
| 1.34 | Ethyl | 1 | H | 2-Propyl | H | H | 3,4,5-T | Resin |
| 1.35 | Ethyl | 1 | H | 2-Propyl | H | H | 3-MeO-benzyl | 97–99 |
| 1.36 | Ethyl | 1 | H | 2-Propyl | H | (S)-Me | Phenyl | 177–178 |
| 1.37 | Ethyl | 1 | H | 2-Propyl | H | Phenyl | Phenyl | 188–189 |
| 1.38 | Ethyl | 1 | H | 2-Propyl | H | (R)-Me | Phenyl | 177–178 |
| 1.39 | Ethyl | 1 | H | 2-Propyl | H | H | 2,3-D | 95–96 |
| 1.40 | Ethyl | 1 | H | 2-Propyl | H | H | 4-MeO-benzyl | 106–107 |
| 1.41 | Ethyl | 1 | H | 2-Propyl | H | H | 3,5-D | 85–87 |
| 1.42 | Ethyl | 1 | H | 2-Propyl | H | H | 2,5-D | 85–87 |
| 1.43 | Methyl | 1 | Tetramethylene | | H | Phenyl | Phenyl | 242–243 |
| 1.44 | Methyl | 1 | H | Ethyl | H | (R)-Me | Phenyl | 116–117 |
| 1.45 | Methyl | 1 | H | Ethyl | H | (S)-Me | Phenyl | 115–117 |
| 1.46 | Methyl | 1 | Me | Methyl | H | Methyl | Phenyl | 120–121 |
| 1.47 | Methyl | 1 | Me | Methyl | H | Phenyl | Phenyl | 173–174 |
| 1.48 | Methyl | 1 | Tetramethylene | | H | Methyl | Phenyl | 163–165 |
| 1.49 | Methyl | 1 | H | Ethyl | H | Phenyl | Phenyl | 190–192 |
| 1.50 | Me₂N | 1 | H | 2-Propyl | H | (R)-Me | Phenyl | 114–115 |
| 1.51 | Me₂N | 1 | H | 2-Propyl | H | (S)-Me | Phenyl | 108–109 |
| 1.52 | Me₂N | 1 | H | 2-Propyl | H | Methyl | 4-Cl-phenyl | 112–113 |
| 1.53 | Me₂N | 1 | H | 2-Butyl | H | H | 4-MeO-benzyl | 85–87 |
| 1.54 | Me₂N | 1 | H | 2-Propyl | H | Methyl | 4-MeO-benzyl | 93–96 |
| 1.55 | Me₂N | 1 | H | 2-Propyl | H | (S)-Me | 4-Me-phenyl | 161–163 |
| 1.56 | Me₂N | 1 | H | 2-Propyl | H | (R)-Me | 4-Me-phenyl | 166–168 |
| 1.57 | Me₂N | 1 | H | 2-Propyl | H | H | 4-MeO-benzyl | 82–83 |
| 1.58 | Me₂N | 1 | H | 2-Propyl | H | H | 3-MeO-benzyl | Resin |
| 1.59 | Me₂N | 1 | H | 2-Butyl | H | H | 3-MeO-benzyl | Resin |
| 1.60 | Me₂N | 1 | H | 2-Propyl | H | Methyl | 4-Fluor-phenyl | 111–112 |
| 1.61 | Me₂N | 1 | H | 2-Propyl | H | H | 3,5-D | Oil |
| 1.62 | Me₂N | 1 | H | 2-Propyl | H | H | 2,5-D | 87–89 |
| 1.63 | Me₂N | 1 | H | 2-Propyl | H | H | 2,3-D | 90–91 |

-continued

| Comp. No. | R₁ | n | R₂ | R₃ | R₄ | R₅ | R₆ | Physical data m.p. °C |
|---|---|---|---|---|---|---|---|---|
| 1.64 | Ethyl | 1 | H | 2-Propyl | H | H | 3-MeO-4-PrO-benzyl | Resin |
| 1.65 | Me₂N | 1 | H | 2-Propyl | H | Methyl | 3,4-D | 105–147 |
| 1.66 | Ethyl | 1 | H | 2-Propyl | H | H | 4-MeO-3-PrO-benzyl | 101–103 |
| 1.67 | Ethyl | 1 | H | 2-Propyl | H | H | 3-MeO-4-AllylO-benzyl | 112–114 |
| 1.68 | Ethyl | 1 | H | 2-Propyl | H | H | 4-MeO-3-AllylO-benzyl | Resin |
| 1.69 | Ethyl | 1 | H | 2-Propyl | H | H | 3-EtO-4-MeO-benzyl | 89–91 |
| 1.70 | Ethyl | 1 | H | 2-Propyl | H | H | 3-MeO-4-PropargylO-benzyl | 109–110 |
| 1.71 | Me₂N | 1 | H | 2-Butyl | H | H | 3-MeO-4-PropargylO-benzyl | Resin |
| 1.72 | Me₂N | 1 | H | 2-Butyl | H | H | 4-MeO-3-PrO-benzyl | Resin |
| 1.73 | Me₂N | 1 | H | 2-Propyl | H | H | 4-MeO-3-Me-benzyl | Resin |
| 1.74 | Me₂N | 1 | H | 2-Propyl | H | H | 3-MeO-4-PropargylO-benzyl | Resin |
| 1.75 | Me₂N | 1 | H | 2-Propyl | H | H | 4-MeO-3-PrO-benzyl | 84–85 |
| 1.76 | Me₂N | 1 | H | 2-Propyl | H | H | 3-MeO-4-AllylO-benzyl | Resin |
| 1.77 | Me₂N | 1 | H | 2-Butyl | H | H | 3-EtO-4-MeO-benzyl | 85–88 |
| 1.78 | Me₂N | 1 | H | 2-Butyl | H | H | 3-MeO-4-AllylO-benzyl | Resin |
| 1.79 | Me₂N | 1 | H | 2-Propyl | H | H | 3-EtO-4-MeO-benzyl | 87–89 |
| 1.80 | Me₂N | 1 | H | 2-Propyl | H | Methyl | 4-Ethyl-phenyl | Resin |
| 1.81 | Ethyl | 1 | H | 2-Propyl | H | H | 4-MeO-3-Me-benzyl | 89–91 |
| 1.82 | Ethyl | 1 | H | 2-Propyl | H | H | 4-EtO-3-MeO-benzyl | 87–89 |
| 1.83 | Me₂N | 1 | H | 2-Propyl | H | H | 4-EtO-3-MeO-benzyl | 84–86 |
| 1.84 | Ethyl | 1 | H | 2-Propyl | H | Methyl | 3,4-D | 112–160 |
| 1.85 | Ethyl | 1 | H | 2-Propyl | H | H | 1-(3,4-Di-MeO-phenyl)-ethyl | 114–130 |

H-2.1: (R,S)-methanesulfonic acid N-[2-methyl-1-(N-benzyl)-carbamoyl]-propyl-amide [Process a)]

[Compound 2.1]

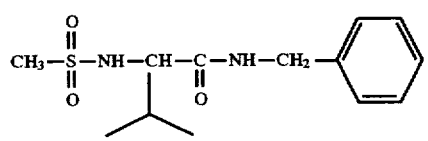

3.9 g of (R,S)-methanesulfonic acid N-(2-methyl-1-carboxy)-propyl-amide and 2.2 ml of N-methylmorpholine are cooled to −20° C. in 100 ml of tetrahydrofuran, while stirring. 2.5 ml of isobutyl chloroformate are added dropwise to this mixture in the course of 5 minutes. The mixture is then subsequently stirred for 30 minutes, the reaction temperature increasing to −10° C. The mixture is then cooled again to −20° C. and 2.2 ml of benzylamine are added dropwise over the course of 5 minutes. The reaction mixture is allowed to warm to room temperature and is stirred for a further 4 hours. It is then introduced in 200 ml of water. The mixture is extracted twice with 400 ml of ethyl acetate each time. The organic phases are washed once with 200 ml of saturated sodium chloride solution, combined, dried over sodium sulfate and concentrated. (R,S)-methanesulfonic acid N-[2-methyl-1-(N-benzyl)-carbamoyl]-propyl-amide, which can be purified by recrystallization from ethyl acetate/hexane, is obtained, melting point 115°–116° C.

The compounds shown in Table 2 are obtained analogously to this example.

TABLE 2

(prepared according to process a))

$$CH_3-\underset{\underset{O}{\|}}{\overset{\overset{O}{\|}}{S}}-NH-\underset{}{\overset{H}{\underset{|}{C}}}-\underset{\underset{O}{\|}}{C}-NH\begin{array}{c}R_4\\\diagup\\\diagdown\\R_6\end{array}R_5$$

Stereochemistry disclosed on the α C atom of the amino acid:

R,S for compounds 2.1 to 2.24, 2.48

S for compounds 2.25 to 2.47, 2.49 to 2.51

| Comp. No. | R₄ | R₅ | R₆ | Physical data |
|---|---|---|---|---|
| 2.1 | H | H | Phenyl | m.p. 115–116° C. |
| 2.2 | H | Methyl | Phenyl | m.p. 132–134° C. |
| 2.3 | Methyl | Methyl | Phenyl | |
| 2.4 | H | H | m-Trifluoromethylphenyl | m.p. 154–155° C. |
| 2.5 | H | Methyl | p-Fluorophenyl | m.p. 106–109° C. |
| 2.6 | H | Methyl | p-Chlorophenyl | m.p. 150–156° C. |
| 2.7 | H | Methyl | p-Methoxyphenyl | |
| 2.8 | H | Methyl | m-Methoxyphenyl | |
| 2.9 | H | Methyl | m-Trifluoromethyl | |
| 2.10 | H | Methyl | Benzyl | |
| 2.11 | H | Methyl | p-Chlorobenzyl | |
| 2.12 | H | Methyl | 2,5-Dimethoxy-4-methylbenzyl | |
| 2.13 | Methyl | Methyl | Benzyl | |
| 2.14 | Methyl | Methyl | p-Fluorobenzyl | |
| 2.15 | Methyl | Methyl | p-Chlorobenzyl | |
| 2.17 | H | Phenyl | Phenyl | m.p. 190–191° C. |
| 2.18 | H | Phenyl | p-Chlorophenyl | |
| 2.19 | H | Phenyl | p-Methoxyphenyl | |
| 2.20 | H | Phenyl | p-Methylphenyl | |
| 2.21 | H | Phenyl | 3,5-di-Trifluoromethylphenyl | |
| 2.22 | H | H | 1-Phenylethyl | |
| 2.23 | H | H | 1-(4-Chlorophenyl)-ethyl | |
| 2.24 | H | H | 2-(4-Chlorophenyl)-propyl | |
| 2.25 | H | H | Phenyl | |
| 2.26 | H | Methyl | Phenyl | |
| 2.27 | Methyl | Methyl | Phenyl | |
| 2.28 | H | H | m-Trifluoromethylphenyl | |
| 2.29 | H | Methyl | p-Fluorophenyl | |
| 2.30 | H | Methyl | p-Chlorophenyl | m.p. 139–142° C. |
| 2.31 | H | Methyl | p-Methoxyphenyl | |
| 2.32 | H | Methyl | m-Methoxyphenyl | |
| 2.33 | H | Methyl | m-Trifluoromethyl | |
| 2.34 | H | Methyl | Benzyl | |
| 2.35 | H | Methyl | p-Chlorobenzyl | |
| 2.36 | H | Methyl | 2,5-Dimethoxy-4-methylbenzyl | |
| 2.37 | Methyl | Methyl | Benzyl | |
| 2.38 | Methyl | Methyl | p-Fluorobenzyl | |
| 2.39 | Methyl | Methyl | p-Chlorobenzyl | |
| 2.40 | H | Phenyl | Phenyl | m.p. 191–193° C. |
| 2.41 | H | Phenyl | p-Chlorophenyl | |
| 2.42 | H | Phenyl | p-Methoxyphenyl | |
| 2.43 | H | Phenyl | p-Methylphenyl | |
| 2.44 | H | Phenyl | 3,5-di-Trifluoromethylphenyl | |
| 2.45 | H | H | 1-Phenylethyl | |
| 2.46 | H | H | 1-(4-Chlorophenyl)-ethyl | |
| 2.47 | H | H | 2-(4-Chlorophenyl)-propyl | |
| 2.48 | H | H | p-Nitrophenyl | m.p. 167–168° C. |
| 2.49 | H | H | o-Trifluoromethylphenyl | m.p. 168–169° C. |
| 2.50 | H | (R)-Me | Phenyl | m.p. 139–142° C. |
| 2.51 | H | (S)-Me | Phenyl | m.p. 138–139° C. |

H-3.1: (S)-2-(N,N-dimethylsulfamoyl)-amino-3-methyl-butyric acid N-[2-(3,4-dimethoxyphenyl)-ethyl]-amide [Process b)]

[Compound 3.1]

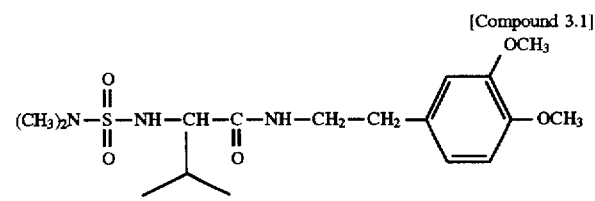

7.2 g of (S)-2-amino-3-methyl-butyric acid N-[2-(3,4-dimethoxyphenyl)-ethyl]-amide and 4 ml of triethylamine are initially introduced in 120 ml of 1,4-dioxane at room temperature, while stirring. 2.8 ml of N,N-dimethylsulfamoyl chloride are added dropwise in the course of 5 minutes. The reaction mixture is then stirred at room temperature for 20 hours and subsequently introduced into 80 ml of 2N hydrochloric acid. The mixture is extracted twice with 200 ml of ethyl acetate each time. The organic phases are washed once with 80 ml of 2N hydrochloric acid, once with 80 ml of saturated sodium chloride solution, once with 80 ml of 5% sodium bicarbonate solution and once with 80 ml of saturated sodium chloride solution, combined, dried over sodium sulfate and concentrated. (S)-2-(N,N-dimethylsulfamoyl)-amino-3-methyl-butyric acid N-[2-(3,4-dimethoxyphenyl)-ethyl]-amide, which can be purified by recrystallization from ethyl acetate/hexane, is obtained, melting point 97°–99° C.

The compounds shown in Table 3 and Table 3a are obtained analogously to this example.

TABLE 3

(prepared according to process b))

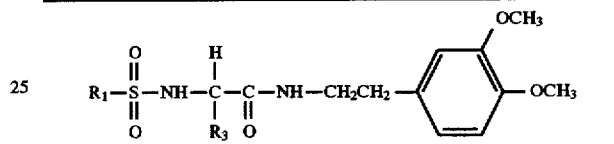

Stereochemistry on the α C atom of the amino acid: S

| Comp. No. | R₁ | R₃ | Physical data |
|---|---|---|---|
| 3.1 | NMe₂ | 2-Propyl | m.p. 97–99° C. |
| 3.2 | NMe₂ | 2-Butyl | m.p. 91–92° C. |
| 3.3 | NMe₂ | 2-Methyl-propyl | Resin |
| 3.4 | NMe₂ | 2-MeS-ethyl | Resin |
| 3.5 | NMe₂ | Hydroxymethyl | |
| 3.6 | NMe₂ | 1-Hydroxy-ethyl | Resin |
| 3.7 | NMeEt | 2-Propyl | m.p. 76–78° C. |
| 3.8 | NMeEt | 2-Butyl | |
| 3.9 | NEt₂ | 2-Propyl | m.p. 95–96° C. |
| 3.10 | NEt₂ | 2-Butyl | m.p. 63–69° C. |
| 3.11 | pyrrolidinyl | 2-Propyl | m.p. 76–77° C. |
| 3.12 | pyrrolidinyl | 2-Butyl | |
| 3.13 | Methyl | 2-Propyl | m.p. 130–132° C. |
| 3.14 | Methyl | 2-Butyl | m.p. 147–148° C. |
| 3.15 | Methyl | 2-Methyl-propyl | Resin |
| 3.16 | Methyl | 2-MeS-ethyl | m.p. 126–127° C. |
| 3.17 | Methyl | Hydroxymethyl | |
| 3.18 | Methyl | 1-Hydroxy-ethyl | m.p. 140–141° C. |
| 3.19 | Ethyl | 2-Propyl | m.p. 148–152° C. |
| 3.20 | Ethyl | 2-Butyl | m.p. 137–138° C. |
| 3.21 | Ethyl | 2-Methyl-propyl | Resin |
| 3.22 | Ethyl | 2-MeS-ethyl | m.p. 79–81° C. |
| 3.23 | Ethyl | Hydroxymethyl | |
| 3.24 | Ethyl | 1-Hydroxy-ethyl | m.p. 82–83° C. |
| 3.25 | Propyl | 2-Propyl | m.p. 108–109° C. |
| 3.26 | Propyl | 2-Butyl | m.p. 95–96° C. |
| 3.27 | 2-Propyl | 2-Propyl | |
| 3.28 | 2-Propyl | 2-Butyl | |
| 3.29 | Butyl | 2-Propyl | m.p. 81–84° C. |
| 3.30 | Butyl | 2-Butyl | m.p. 105–106° C. |
| 3.31 | 2-Butyl | 2-Propyl | |
| 3.32 | 2-Butyl | 2-Butyl | |
| 3.33 | 2-Methyl-propyl | 2-Propyl | |

-continued

| Comp. No. | R₁ | R₃ | Physical data |
|---|---|---|---|
| 3.34 | 2-Methyl-propyl | 2-Butyl | |
| 3.35 | 2-Methyl-2-propyl | 2-Propyl | |
| 3.36 | 2-Methyl-2-propyl | 2-Butyl | |
| 3.37 | Pentyl | 2-Propyl | |
| 3.38 | Hexyl | 2-Propyl | |
| 3.39 | Octyl | 2-Propyl | m.p. 77–78° C. |
| 3.40 | Decyl | 2-Propyl | m.p. 106–107° C. |
| 3.41 | Dodecyl | 2-Propyl | |
| 3.42 | Vinyl | 2-Propyl | m.p. 136–137° C. |
| 3.43 | Vinyl | 2-Butyl | m.p. 149–150° C. |
| 3.44 | Vinyl | 2-Methyl-propyl | Resin |
| 3.45 | Vinyl | 2-MeS-ethyl | m.p. 129–130° C. |
| 3.46 | Vinyl | Hydroxymethyl | |
| 3.47 | Vinyl | 1-Hydroxy-ethyl | m.p. 134–135° C. |
| 3.48 | Trifluoromethyl | 2-Propyl | m.p. 120–121° C. |
| 3.49 | Trifluoromethyl | 2-Butyl | |
| 3.50 | Chloromethyl | 2-Propyl | m.p. 131–132° C. |
| 3.51 | Chloromethyl | 2-Butyl | |
| 3.52 | Dichloromethyl | 2-Propyl | |
| 3.53 | Dichloromethyl | 2-Butyl | |
| 3.54 | Trichloromethyl | 2-Propyl | |
| 3.55 | Trichloromethyl | 2-Butyl | |
| 3.56 | 2,2,2-Trifluoromethyl | 2-Propyl | |
| 3.57 | 2,2,2-Trifluoromethyl | 2-Butyl | |
| 3.58 | 3-Chloropropyl | 2-Propyl | m.p. 117–118° C. |
| 3.59 | 3-Chloropropyl | 2-Butyl | |
| 3.60 | 2-Methoxy-ethyl | 2-Propyl | |
| 3.61 | 2-Methoxy-ethyl | 2-Butyl | |
| 3.62 | 2-Methanesulfonyl-ethyl | 2-Propyl | |
| 3.63 | 2-Methanesulfonyl-ethyl | 2-Butyl | |
| 3.64 | Methylsulfonyl-methyl | 2-Propyl | m.p. 136–137° C. |
| 3.65 | 2,2,2-Trifluoroethyl | 2-Propyl | m.p. 143–144° C. |
| 3.66 | NH₂ | 2-Propyl | m.p. 136–137° C. |
| 3.67 | NH₂ | 2-Butyl | m.p. 137–138° C. |
| 3.68 | NH(CH₃) | 2-Propyl | m.p. 133–136° C. |
| 3.69 | NH(CH₃) | 2-Butyl | m.p. 142–144° C. |
| 3.70 | NH(Ethyl) | 2-Propyl | m.p. 105–106° C. |
| 3.71 | NH(Ethyl) | 2-Butyl | m.p. 104–105° C. |

TABLE 3a (prepared according to process b))

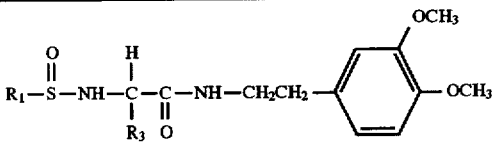

Stereochemistry on the α C atom of the amino acid: S

| Comp. No. | R₁ | R₃ | Physical data |
|---|---|---|---|
| 3.90 | 2-Propyl | 2-Propyl | Resin |
| 3.91 | 2-Butyl | 2-Propyl | Resin |
| 3.92 | 2-Butyl | 2-Butyl | Resin |
| 3.93 | 2-Methyl-propyl | 2-Propyl | m.p. 113–114° C. |
| 3.94 | 2-Methyl-propyl | 2-Butyl | m.p. 102–103° C. |
| 3.95 | Pentyl | 2-Propyl | m.p. 91–92° C. |
| 3.96 | Pentyl | 2-Butyl | m.p. 74–75° C. |
| 3.97 | Hexyl | 2-Propyl | m.p. 94–95° C. |
| 3.98 | Hexyl | 2-Butyl | m.p. 99–100° C. |
| 3.99 | Cyclohexyl | 2-Propyl | Resin |
| 3.100 | Cyclopentyl | 2-Propyl | Resin |
| 3.101 | Cyclopentyl | 2-Butyl | Resin |
| 3.102 | Cyclohexyl | 2-Butyl | Resin |
| 3.103 | 2-(MeO-carbonyl)-ethyl | 2-Propyl | m.p. 121–123° C. |

H-6.1: (S)-2(isopropylsulfonyl)-amino-3-methyl-butyric acid -N-[2-(3,4-dimethoxyphenyl)-ethyl]-amide [Process c)]

[Compound 6.1]

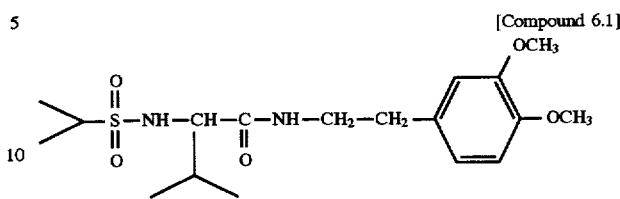

3.7 g of (S)-2-(isopropylsulfinyl)-amino-3-methyl-butyric acid N-[2-(3,4-dimethoxyphenyl)-ethyl]-amide (Example 3.90) are dissolved in 50 ml of acetone at room temperature. An acetone solution saturated with potassium permanganate is added dropwise to this stirred solution until the reaction mixture retains the violet colour of the permanganate; the reaction mixture is then stirred at room temperature for 45 minutes. The resulting manganese dioxide is removed by filtration over Celite. The filtrate is evaporated to dryness and the resulting residue is dissolved in 500 ml of methyl acetate. This organic phase is washed once with 200 ml of water, dried over sodium sulfate and concentrated. The resulting residue is chromatographed over silica gel with a mixture of one part of methyl acetate and one part of n-hexane. (S)-2-(isopropylsulfonyl)-amino-3-methyl-butyric acid N-[2-(3,4-dimethoxyphenyl)-ethyl]-amide, which can be further purified by recrystallization from methyl acetate/n-hexane, is obtained, melting point 86°–87° C.

The compounds shown in Table 6 are obtained analogously to this example.

TABLE 6

(prepared according to process c))

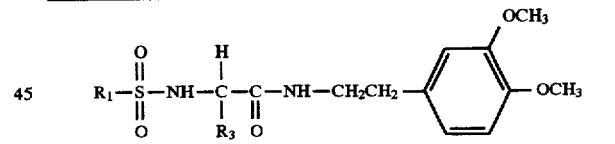

Stereochemistry on the α C atom of the amino acid: S

| Comp. No. | R₁ | R₃ | Physical data |
|---|---|---|---|
| 6.1 | 2-Propyl | 2-Propyl | m.p. 86–87° C. |
| 6.2 | 2-Butyl | 2-Propyl | m.p. 92–93° C. |
| 6.3 | 2-Butyl | 2-Butyl | Resin |
| 6.4 | 2-Methyl-propyl | 2-Propyl | m.p. 78–80° C. |
| 6.5 | 2-Methyl-propyl | 2-Butyl | m.p. 74–76° C. |
| 6.6 | Pentyl | 2-Propyl | m.p. 95–96° C. |
| 6.7 | Pentyl | 2-Butyl | m.p. 96–97° C. |
| 6.8 | Hexyl | 2-Propyl | m.p. 102–103° C. |
| 6.9 | Hexyl | 2-Butyl | m.p. 102–103° C. |
| 6.10 | Cyclohexyl | 2-Propyl | Resin |
| 6.11 | Cyclopentyl | 2-Propyl | Resin |
| 6.12 | Cyclopentyl | 2-Butyl | Resin |
| 6.13 | Cyclohexyl | 2-Butyl | Resin |
| 6.14 | 2-(MeO-carbonyl)-ethyl | 2-Propyl | 98–99° C. |

Preparation Example for Intermediates

Z-1.1: (S)-2-amino-3-methyl-butyric acid N-[2-(3,4-dimethoxyphenyl)-ethyl]-amide

[Compound 4.1]

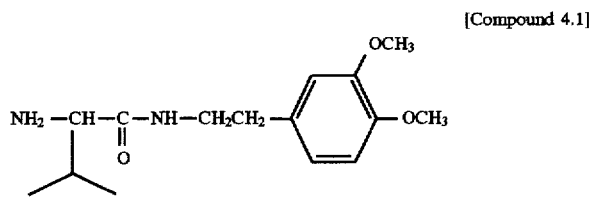

23.8 g of (S)-2-[(1,1-dimethylethyl)-oxycarbonyl]-amino-3-methyl-butyric acid N-[2-(3,4-dimethoxyphenyl)]-ethyl-amide are stirred at room temperature together with 700 ml of 4N hydrochloric acid for 24 hours. The reaction mixture is extracted twice with 250 ml of ethyl acetate each time; the organic phases are rinsed once with 200 ml of 2N hydrochloric acid and then discarded. The combined aqueous phases are first brought to about pH 6 with solid sodium hydroxide and then brought to pH greater than 8 with solid potassium carbonate. The aqueous phase is subsequently saturated with sodium chloride and extracted twice with 500 ml of ethyl acetate each time. The organic phases are rinsed once with 200 ml of saturated sodium chloride solution, combined, dried over potassium carbonate and concentrated. (S)-2-amino-3-methyl-butyric acid N-[2-(3,4-dimethoxyphenyl)-ethyl]-amide, which can be purified by recrystallization from ethyl acetate/hexane, is obtained; melting point 52°–54° C.

The intermediates shown in Table 4 are obtained analogously to this example.

TABLE 4

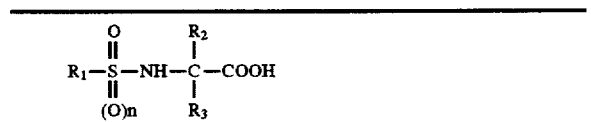

Stereochemistry on the α C atom of the amino acid: S

| Comp. No. | $R_2$ | $R_3$ | $R_4$ | $R_5$ | $R_6$ | Physical data |
|---|---|---|---|---|---|---|
| 4.1 | H | 2-Propyl | H | H | 3,4-Dimethoxybenzyl | m.p. 52–54° C. |
| 4.2 | H | 2-Butyl | H | H | 3,4-Dimethoxybenzyl | m.p. 86–88° C. |
| 4.3 | H | 2-Methylpropyl | H | H | 3,4-Dimethoxybenzyl | m.p. 70–72° C. |
| 4.4 | H | 2-Methylthio-ethyl | H | H | 3,4-Dimethoxybenzyl | Resin |
| 4.5 | H | Hydroxymethyl | H | H | 3,4-Dimethoxybenzyl |  |
| 4.6 | H | 1-Hydroxyethyl | H | H | 3,4-Dimethoxybenzyl | m.p. 112–113° C. |

Z-2.1 (R,S)-methanesulfonic acid N-(2-methyl-1-carboxy)-propyl-amide

[Compound 5.1]

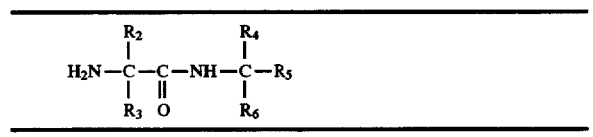

30 g of D,L-valine and 10.2 g of sodium hydroxide are dissolved in 250 ml of water and the solution is cooled to 0° C., while stirring. A solution of 10.2 g of sodium hydroxide in 250 ml of water and 20 ml of methanesulfonyl chloride in 250 ml of toluene are simultaneously added dropwise to this solution during the course of, in each case, one hour. The reaction mixture is first further stirred at 0° C. for 2 hours and then further stirred at room temperature for 16 hours. The toluene phase is subsequently separated off in a separating funnel and discarded. The aqueous phase is brought to pH less than 3 with concentrated hydrochloric acid. It is extracted twice with 1000 ml of diethyl ether each time. The organic phases are washed twice with 200 ml of saturated sodium chloride solution each time, combined, dried over magnesium sulfate and concentrated. (R,S)-methanesulfonic acid N-(2-methyl-1-carboxy)-propyl-amide, which can be purified by recrystallization from ethyl acetate/hexane, is obtained, melting point 90°–91° C.

The intermediates shown in Table 5 are obtained analogously to this example.

TABLE 5

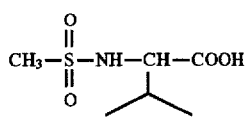

Stereochemistry disclosed on the α C atom of the amino acid:

| Comp. No. | $R_1$ | n | $R_2$ | $R_3$ | Physical data |
|---|---|---|---|---|---|
| 5.1 | Methyl | 1 | H | 2-Propyl | m.p. 90–91° C. |
| 5.2 | Methyl | 1 | H | 2-Propyl | Oil |
| 5.3 | Me$_2$N— | 1 | H | 2-Propyl | Oil |
| 5.4 | Me$_2$N— | 1 | H | 2-Propyl | Resin |
| 5.5 | Methyl | 0 | H | 2-Propyl |  |
| 5.6 | 2-Propyl | 0 | H | 2-Propyl |  |
| 5.7 | 2-Methyl-2-propyl | 0 | H | 2-Propyl |  |
| 5.8 | Methyl | 0 | H | 2-Propyl |  |
| 5.9 | 2-Propyl | 0 | H | 2-Propyl |  |
| 5.10 | 2-Methyl-2-propyl | 0 | H | 2-Propyl |  |
| 5.11 | Ethyl | 1 | H | 2-Propyl | Resin |
| 5.12 | Me$_2$N | 1 | H | 2-Butyl | Resin |
| 5.13 | Ethyl | 1 | H | 1-(2-Me-2-Pr)—O-ethyl | Oil |
| 5.14 | Methyl | 1 | H | Ethyl | Resin |
| 5.15 | Ethyl | 1 | H | Ethyl | Resin |
| 5.16 | Methyl | 1 | Me | Methyl | m.p. 109–111° C. |
| 5.17 | Methyl | 1 | Tetramethylene | | m.p. 133–135° C. |

2. Formulation Examples for active ingredients of the Formula I (%=per cent by weight)

| F-2.1. Wettable powder | a) | b) | c) |
|---|---|---|---|
| Active ingredient from Tables 1, 2, 3, 3a and 6 | 25% | 50% | 75% |
| Sodium ligninsulfonate | 5% | 5% | — |
| Sodium laurylsulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silicic acid | 5% | 10% | 10% |
| Kaolin | 62% | 27% | — |

The active ingredient is mixed thoroughly with the additives and the mixture is ground thoroughly in a suitable mill.

Wettable powders can be diluted with water to give suspensions of any desired concentration are obtained.

| F-2.2. Emulsion concentrate | |
|---|---|
| Active ingredient from Tables 1, 2, 3, 3a and 6 | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 34% |
| Xylene mixture | 50% |

Emulsions of any desired concentration can be prepared from this concentrate by dilution with water.

| F-2.3. Dust | a) | b) |
|---|---|---|
| Active ingredient from Tables 1, 2, 3, 3a and 6 | 5% | 8% |
| Talc | 95% | — |
| Kaolin | — | 92% |

Ready-to-use dusts are obtained by mixing the active ingredient with the carrier and grinding the mixture on a suitable mill.

| F-2.4. Extruder granules | |
|---|---|
| Active ingredient from Tables 1, 2, 3, 3a and 6 | 10% |
| Sodium ligninsulfonate | 2% |
| Carboxymethylcellulose | 1% |
| Kaolin | 87% |

The active ingredient is mixed with the additives and the mixture is ground and moistened with water. This mixture is extruded and then dried in a stream of air.

| F-2.5. Coated granules | |
|---|---|
| Active ingredient from Tables 1, 2, 3, 3a and 6 | 3% |
| Polyethylene glycol (MW 200) | 3% |
| Kaolin | 94% |

(MW = molecular weight)

The finely ground active ingredient is applied uniformly to the kaolin, which has been moistened with polyethylene glycol, in a mixer. Dust-free coated granules are obtained in this manner.

| F-2.6. Suspension concentrate | |
|---|---|
| Active ingredient from Tables 1, 2, 3, 3a and 6 | 40% |
| Ethylene glycol | 10% |
| Nonylphenol polyethylene glycol ether (15 mol of ethylene oxide) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. A suspension concentrate from which suspensions of any desired dilution can be prepared by dilution with water is thus obtained.

BIOLOGICAL EXAMPLES

B-1: Action against Plasmopara viticola on vines a) Residual protective action

Vine seedlings in the 4–5 leaf stage are sprayed with a spray mixture prepared from a wettable powder of the active ingredient (0.02% of active substance). After 24 hours, the treated plants are infected with a sporangia suspension of the fungus. After incubation for 6 days at 95–100% relative atmospheric humidity and 20° C., the fungal infestation is evaluated.

Active ingredients No. 1.2, 3.1, 3.19, 3.25, 3.29 and others achieve complete suppression of the fungal infestation (residual infestation 0 to 10%). In contrast, untreated but infected control plants show a Plasmopara infestation of 100%.

B-2: Action against Phytophthora on tomato plants a) Residual protective action

After growing for 3 weeks, tomato plants are sprayed with a spray mixture prepared from a wettable powder of the active ingredient (0.02% of active substance). After 48 hours, the treated plants are infected with a sporangia suspension of the fungus. The fungal infestation is evaluated after incubation of the infected plants for 4 days at 90–100% relative atmospheric humidity and 20° C.

b) Systemic action

After growing for three weeks, a spray mixture prepared from a wettable powder of the active ingredient (0.02% of active substance, based on the soil volume) is added to tomato plants. It is ensured that the spray mixture does not come into contact with the above-ground parts of the plant. After 4 days, the treated plants are infected with a sporangia suspension of the fungus. The fungal infestation is evaluated after incubation of the infected plants for 4 days at 90–100% relative atmospheric humidity and 20° C.

Infestation is prevented practically completely (0 to 5% infestation) with compounds No. 3.1, 3.19, 3.25, 3.29 and others. In contrast, untreated but infected control plants show a Phytophthora infestation of 100%.

B-3: Residual protective action against Cercospora arachidicola on groundnuts

Groundnut plants 10 to 15 cm high are sprayed dripping wet with an aqueous spray mixture (0.02% of active substance) and infected with a conidia suspension of the fungus for 48 hours. The plants are incubated for 72 hours at 21° C. and high atmospheric humidity and then placed in a greeenhouse until the typical leaf spots appear. The action of the active substance is evaluated 12 days after infection on the basis of the number and size of the leaf spots. Active ingredients of the formula I cause a reduction in the leaf spots to below about 10% of the leaf surface. The disease is completely suppressed (0–5% infestation) in some cases.

B-4: Action against Puccinia graminis on wheat a) Residual protective action 6 days after sowing, wheat plants are sprayed dripping wet with an aqueous spray mixture (0.02% of active substance), and infected 24 hours later with a uredospore suspension of the fungus. After an incubation time of 48 hours (conditions: 95–100% relative atmospheric humidity at 20° C.), the plants are placed in a greenhouse at 22° C. The rust pustule development is evaluated 12 days after infection.

b) Systemic action 5 days after sowing, wheat plants are watered with an aqueous spray mixture (0.006% of active substance, based on the soil volume). It is ensured that the spray mixture does not come into contact with the above-ground parts of the plants. 48 hours later, the plants are infected with a uredospore suspension of the fungus. After the incubation time of 48 hours (conditions: 95 to 100% relative atmospheric humidity at 20° C.), the plants are placed in a greenhouse at 22° C. The rust pustule development is evaluated 12 days after infection.

Compounds of the formula I cause a significant reduction in fungal attack, in some cases to 10–0%.

B-5: Residual protective action against Venturia inaequalis on apples

Apple seedlings with fresh shoots 10 to 20 cm long are sprayed dripping wet with a spray mixture (0.02% of active substance), and infected with a conidia suspension of the fungus 24 hours later. The plants are incubated for 5 days at 90–100% relative atmospheric humidity, and placed in a greenhouse at 20°–24° C. for a further 10 days. The scab infestation is evaluated 15 days after infection. Compounds of the formula I from one of the Tables 1, 2, 3, 3a and 6 chiefly display a lasting action against scab diseases (less than 10% infestation).

B-6: Residual protective action against Erysiphe graminis on barley

Barley plants about 8 cm high are sprayed dripping wet with a spray mixture (0.02% of active substance) and dusted with conidia of the fungus 3 to 4 hours later. The infected plants are placed in a greenhouse at 22° C. The fungal attack is evaluated 10 days after infection. Compounds of the formula I generally are capable of suppressing the disease infestation to less than 20%, and in some cases also completely.

B-7: residual protective action against Botyris cinerea on apple fruit

Artificially damaged apples are treated by dripping a spray mixture (0.02% of active substance) onto the damaged areas. The treated fruit is then inoculated with a spore suspension of the fungus and incubated for one week at high atmospheric humidity and 20° C. The fungicidal action of the test substance is deduced from the number of superficially rotted damaged areas. Active ingredients of the formula I from Tables 1, 2, 3, 3a and 6 are capable of preventing the spread of the rot, in some cases completely.

B-8: Action against Rhizoctonia solani on rice a) Protective local soil application Rice plants 10 days old are thoroughly watered with a suspension (spray mixture) prepared from the formulated test substance without above-ground pans of the plants being contaminated. Infection is carried out 3 days later by placing one barley straw infected with Rhizoctonia solani between the rice plants per pot. After incubation in a climatically controlled room at a day-time temperature of 29° C. and a night-time temperature of 26° C. and 95% relative atmospheric humidity for 6 days, the fungal infestation is evaluated. Less than 5% of the rice plants showed an infestation. The plants had a healthy appearance.

b) Protective local leaf application

Rice plants 12 days old are sprayed with a suspension prepared from the formulated test substance. Infection is carried out one day later by placing one barley straw infected with Rhizoctonia solani between the rice plants per pot. After incubation in a climatically controlled room at a day-time temperature of 29° C. and a night-time temperature of 26° C. and 95% relative atmospheric humidity for 6 days, rating is carried out. Untreated but infected control plants show a fungal infestation of 100%. Compounds of the formula I in some cases cause an almost complete inhibition of the disease infestation.

B-9: Action against Helminthosporium gramineum

Wheat grains are contaminated with a spore suspension of the fungus and left to dry. The contaminated grains are dressed with a suspension of the test substance (600 ppm of active ingredient, based on the weight of the seeds). After 2 days, the grains are laid out on suitable agar dishes, and after a further 4 days the development of the fungal colonies around the grains is evaluated. The number and size of fungal colonies are used to evaluate the test substance. Compounds of the formula I in some cases show a very good action, i.e. complete inhibition of the fungal colonies.

B-10: Action against Pythium debaryanum on sugar beet

The fungus is cultured from sterile oat grains and added to a soil/sand mixture. The soil thus infected is introduced into flowerpots and sown with sugar beet seeds. Immediately after sowing, the test preparations, formulated as wettable powders, are poured over the soil as an aqueous suspension (20 ppm of active ingredient, based on the soil volume). The pots are then placed in a greenhouse at 20°–24° C. for 2–3 weeks. The soil is constantly kept uniformly moist by gentle spraying with water. For evaluation of the tests, the emergence of the sugar beet plants and the proportion of healthy and sick plants are determined. After treatment with active ingredients of the formula I, more than 80% of the plants emerge and have a healthy appearance. In the control pots, only isolated emerged plants with a sickly appearance are observed.

What is claimed is:

1. A process for the preparation of a compound of the formula 1:

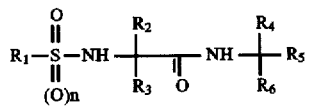

in which n is the number zero or one;

$R_1$ is $C_1$–$C_{12}$alkyl, which is unsubstituted or can be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$halogenoalkyl or a group $NR_{13}R_{14}$; in which $R_{13}$ and $R_{14}$ independently of one another are hydrogen or $C_1$–$C_6$alkyl or together are tetra- or pentamethylene;

$R_2$ and $R_3$ independently of one another are hydrogen; $C_1$–$C_8$alkyl; $C_1$–$C_8$alkyl which is substituted by hydroxyl, $C_1$–$C_4$alkoxy, mercapto or $C_1$–$C_4$alkylthio; $C_3$–$C_8$alkenyl;

$C_3$–$C_8$alkynyl; $C_3$–$C_8$cycloalkyl or $C_3$–$C_8$cycloalkyl-$C_1$–$C_4$alkyl, or in which the two groups $R_2$ and $R_3$, together with the carbon atom to which they are bonded, form a three- to eight-membered carbocyclic ring;

$R_4$ is hydrogen or $C_1$–$C_6$alkyl;

$R_5$ is hydrogen; $C_1$–$C_6$alkyl or phenyl, which is unsubstituted or can be substituted by halogen, nitro, $C_1$–$C_4$alkyl, $C_1$–$C_4$halogenoalkyl, $C_1$–$C_4$alkoxy or $C_1$–$C_4$alkylthio; and $R_6$ is a group G

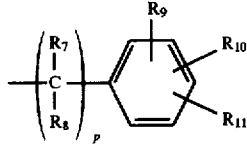

in which $R_7$ and $R_8$ independently of one another are hydrogen or $C_1$–$C_6$alkyl;

p is the number zero or one; and $R_9$, $R_{10}$ and $R_{11}$ independently of one another are hydrogen, $C_1$–$C_6$alkyl, $C_1$–$C_6$halogenoalkyl, $C_3$–$C_6$alkenyl, $C_3$–$C_6$alkynyl, $C_1$–$C_6$alkoxy, $C_3$–$C_6$alkenyloxy, $C_3$–$C_6$alkynyloxy, $C_1$–$C_6$alkylthio, halogen or nitro, which comprises a) allowing a substituted amino acid of the formula II

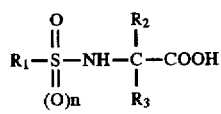

to react with an amine of the formula III

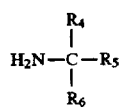

with or without a diluent, in the presence or absence of an acid-binding agent, at temperatures of $-80°$ C. to $150°$ C., or b) allowing a sulfonic acid derivative or sulfinic acid derivative of the formula IV

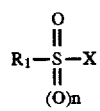

to react with an amine of the formula V

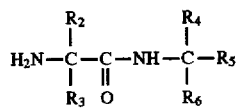

with or without a diluent, in the presence or absence of an acid-binding agent, at temperatures of $-80°$ C. to $150°$ C., or c) oxidizing a compound of the formula I′

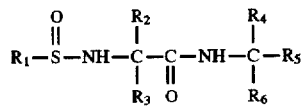

with an oxidizing agent, with or without a diluent, in the presence or absence of an acid or base, at temperatures of between $-80°$ C. and $150°$ C., in which, in formulae II, III, IV, V and I′, the substituents $R_1$, $R_2$, $R_3$, $R_4$, $R_5$, $R_6$ and n are as defined in formula I and X is halogen, $R_1$—$SO_2$—O— or $R_1$—SO—O—.

2. A composition for controlling and preventing infestation of plants by microorganisms, which comprises a compound of the formula I as the active ingredient:

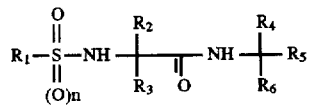

in which n is the number zero or one;

$R_1$ is $C_1$–$C_{12}$alkyl, which is unsubstituted or can be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_3$–$C_6$alkynyloxycarbonyl; $C_3$–$C_8$cycloalkyl; $C_2$–$C_{12}$alkenyl;

$C_2$–$C_{12}$alkynyl; $C_1$–$C_{12}$halogenoalkyl or a group $NR_{13}R_{14}$; in which $R_{13}$ and $R_{14}$ independently of one another are hydrogen or $C_1$–$C_6$alkyl or together are tetra- or pentamethylene;

$R_2$ and $R_3$ independently of one another are hydrogen; $C_1$–$C_8$alkyl; $C_1$–$C_8$alkyl which is substituted by hydroxyl, $C_1$–$C_4$alkoxy, mercapto or $C_1$–$C_4$alkylthio; $C_3$–$C_8$alkenyl;

$C_3$–$C_8$alkynyl; $C_3$–$C_8$cycloalkyl or $C_3$–$C_8$cycloalkyl-$C_1$–$C_4$alkyl, or in which the two groups $R_2$ and $R_3$, together with the carbon atom to which they are bonded, form a three- to eight-membered carbocyclic ring;

$R_4$ is hydrogen or $C_1$–$C_6$alkyl;

$R_5$ is hydrogen; $C_1$–$C_6$alkyl or phenyl, which is unsubstituted or can be substituted by halogen, nitro, $C_1$–$C_4$alkyl, $C_1$–$C_4$halogenoalkyl, $C_1$–$C_4$alkoxy or $C_1$–$C_4$alkylthio; and $R_6$ is a group G

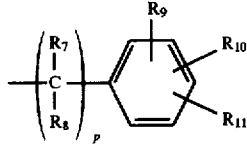

in which $R_7$ and $R_8$ independently of one another are hydrogen or $C_1$–$C_6$alkyl;

p is the number zero or one; and $R_9$, $R_{10}$ and $R_{11}$ independently of one another are hydrogen, $C_1$–$C_6$alkyl, $C_1$–$C_6$halogenoalkyl, $C_3$–$C_6$alkenyl, $C_3$–$C_6$alkynyl, $C_1$–$C_6$alkoxy, $C_3$–$C_6$alkenyloxy, $C_3$–$C_6$alkynyloxy, $C_1$–$C_6$alkylthio, halogen or nitro, together with a suitable carrier material.

3. A method of controlling and preventing infestation of plants by microorganisms, which comprises applying, as the active ingredient, a compound of the formula I:

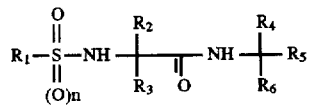

in which n is the number zero or one;

$R_1$ is $C_1$–$C_{12}$alkyl, which is unsubstituted or can be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl or $C_3$–$C_6$alkynyloxycarbonyl; $C_3$–$C_8$cycloalkyl; $C_2$–$C_{12}$alkenyl;

$C_2$–$C_{12}$alkynyl; $C_1$–$C_{12}$halogenoalkyl or a group $NR_{13}R_{14}$; in which $R_{13}$ and $R_{14}$ independently of one another are hydrogen or $C_1$–$C_6$alkyl or together are tetra- or pentamethylene;

$R_2$ and $R_3$ independently of one another are hydrogen; $C_1$–$C_8$alkyl; $C_1$–$C_8$alkyl which is substituted by hydroxyl, $C_1$–$C_4$alkoxy, mercapto or $C_1$–$C_4$alkylthio; $C_3$–$C_8$alkenyl;

$C_3$–$C_8$alkynyl; $C_3$–$C_8$cycloalkyl or $C_3$–$C_8$cycloalkyl-$C_1$–$C_4$alkyl, or in which the two groups $R_2$ and $R_3$, together with the carbon atom to which they are bonded, form a three- to eight-membered carbocyclic ring;

$R_4$ is hydrogen or $C_1$–$C_6$alkyl;

$R_5$ is hydrogen; $C_1$–$C_6$alkyl or phenyl, which is unsubstituted or can be substituted by halogen, nitro, $C_1$–$C_4$alkyl, $C_1$–$C_4$halogenoalkyl, $C_1$–$C_4$alkoxy or $C_1$–$C_4$alkylthio; and $R_6$ is a group G

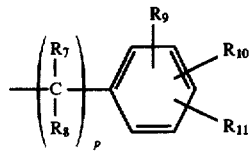

in which $R_7$ and $R_8$ independently of one another are hydrogen or $C_1$–$C_6$alkyl;

p is the number zero or one; and $R_9$, $R_{10}$ and $R_{11}$ independently of one another are hydrogen, $C_1$–$C_6$alkyl, $C_1$–$C_6$halogenoalkyl, $C_3$–$C_6$alkenyl, $C_3$–$C_6$alkynyl, $C_1$–$C_6$alkoxy, $C_3$–$C_6$alkenyloxy, $C_3$–$C_6$alkynyloxy, $C_1$–$C_6$alkylthio, halogen or nitro, to the plants, to the parts of plants or to the nutrient medium of the plants.

\* \* \* \* \*